United States Patent [19]
Senter et al.

[11] Patent Number: 5,338,678
[45] Date of Patent: Aug. 16, 1994

[54] EXPRESSION OF DNA SEQUENCES ENCODING A THERMALLY STABLE CYTOSINE DEAMINASE FROM SACCHAROMYCES

[75] Inventors: Peter D. Senter, Seattle; Peter C. D. Su; Hans Marquardt, both of Mercer Island; Martha S. Hayden; Peter Linsley, both of Seattle, all of Wash.

[73] Assignee: Oncogen, a Limited Partnership, Seattle, Wash.

[21] Appl. No.: 531,646

[22] Filed: Jun. 1, 1990

Related U.S. Application Data

[63] Continuation-in-part of Ser. No. 365,020, Jun. 9, 1989, abandoned.

[51] Int. Cl.$^5$ .......................... C12N 5/00; C12N 1/20; C12N 15/00; C07H 15/12
[52] U.S. Cl. .................. 435/227; 435/240.2; 435/252.3; 435/320.1; 536/23.2; 536/23.74
[58] Field of Search ................ 536/27; 435/69.1, 70.1, 435/70.3, 71.1, 71.2, 183, 195, 227, 252.1, 256

[56] References Cited

PUBLICATIONS

Suggs et al. (1981) Use of synthetic oligonucleotides as hybridization probes . . . 78, 6613–6617.
Katsuragi et al., *Agric. Biol. Chem.* (1989) 53:1313–1319.
Ipata et al., (1971) Biochemistry 10:4270–4276.
Ipata et al., (1978) Meth. Enz. 51:394–401.
Katsuragi et al., (1986) Agric. Biol. Chem. 50:1721–1730.
Katsuragi et al. (1987) *App. Biochem. Biotech.*, 16:61–69.
Kream et al. (1952) *J. Amer. Chem. Soc.*, 74:5157–5160.
McIntosh et al. (1986) *Mol. Cell. Biol.*, 6:1711–1721.
Nishiyama et al. (1985) *Cancer Research*, 45:1753–1761.
O'Donovan et al. (1970) *Bact. Rev.*, 34:278–343.
Sakai et al. (1985) *J. Biotech.*, 2:13–21.
West et al. (1982) *Biochim. Biophys. Acta*, 719:251–258.
Yergatian et al. (1977) *Experientia*, 33:1570–1571.
Yeung et al. (1985) *J. Biol. Chem.*, 260:10299–10307.

Primary Examiner—Elizabeth C. Weimar
Assistant Examiner—Deborah Crouch
Attorney, Agent, or Firm—Reed & Robins

[57] ABSTRACT

Thermally stable cytosine deaminase (CDase), and the gene coding therefor, is disclosed as well as methods of isolating, purifying, and recombinantly producing the same. The thermally stable CDase can be isolated from *Saccharomyces cerevisiae*. The yeast isolated enzyme has a molecular weight of approximately 32 kDa, as determined by gel filtration chromatography, and is composed of two subunits, each with a molecular weight of about 17 kDa. Thermally stable yeast CDase so purified shows no significant sequence homology with other known sequenced proteins.

9 Claims, 10 Drawing Sheets

PRIMER CDA4/RI:       (5'GGGGAATTC--)
    GGT AGA GGT CAC AAC ATG CGT TTC CAA AAG GGT 3'    --->
L   G   R   G   H   N   M   R   F   Q   K   G   S   A   T
    47

L   H   G   E   I   S   T   L   E   N   C   G   R   L   E

G   K   V   Y   K   D   T   T   L   Y   T   T   L   S   P

C   D   M   C   T   G   A   I   I   M   Y   G   I   P   R

C   V   V   G   E   N   V   N   F   K   S   K   G   E   K

Y   L   Q   T   R   G   H   E   V   V   V   D   D   E
                                        147
R   C   K   K   I   M   K   Q   F   I   D   E   R   P   Q
                                            <---3'CTT TCT GGT GTT 157 158
D   W   F   E   D   I   G   E
CTA ACC AAG CTT CTG TAG CCA
  G           A   A         (--CTTAAGGGG 5') PRIMER CDA AS5'
```

```
TTCTCCTCAT ATCACGTGTC ATTCTGCAGG GCGGTAGTAC CGAGACCCTG ACTTTCTTTT    60
TTTTTGCGA AATTAAAAAG TTCATTTTCA ATTCGACAAT GAGATCTACA AGCCATTGTT   120
TTATGTTGAT GAGAGCCAGC TTAAAGAGTT AAAAATTTCA TAGCTAATGG TGACAGGGGG   180
AATGGCAAGC AAGTGGGATC AGAAGGGTAT GGACATTGCC TATGAGGAGG CGGCCTTAGG   240
TTACAAAGAG GGTGGTGTTC CTATTGGCGG ATGTCTTATC AATAACAAAG ACGGAAGTGT   300
TCTCGGTCGT GGTCACAACA AAAGGGTTCC GCCACACTAC ATGGTGAGAT               360
CTCCACTTTG GAAAACTGTG GGAGATTAGA GGGCAAAGTG TACAAAGATA CCACTTTGTA   420
TACGACGCTG TCTCCATGCG ACATGTGTAC AGGTGCCATC ATCATGTATG GTATTCCACG   480
CTGTGTTGTC GGTGAGAACG TTAATTTCAA AAGTAAGGGC GAGAAATATT TACAAACTAG   540
AGGTCACGAG GTTGTTGTTG TTGACGATGA GAGGTGTAAA AAGATCATGA AACAATTAT    600
CGATGAAAGA CCTCAGGATT GGTTTGAAGA TATTGGTGAG TAGAGCACGC AGCACGCGT    660
ATTTACGTAT TTAATTTTAT ATATTTGTGC ATACACTACT AGGGAAGACT TGAAAAAAAC   720
CTAGGAAATG AAAAAACGAC ACAGGAAGTC CCGTATTTAC TATTTTTTCC TTCCTTTTGA   780
TGGGGGCAGGG CGGAAATAGA GGATAGGATA AGCCATCTGC TTAGCTGTTT CCGTCTCATC   840
TTCGGTAGTT GTCTCATGTC GTTCAGTATA CTTAGAGCGC AT                      882
```

FIG. 9

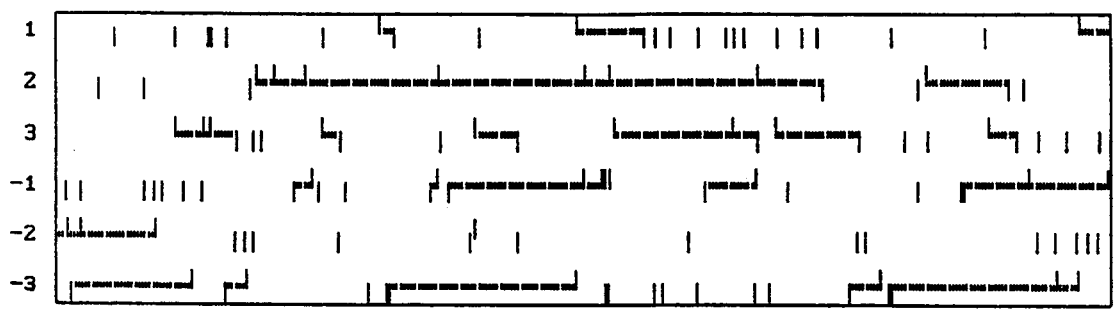

FIG. 10

```
START
ATG GTG ACA GGG GGA ATG GCA AGC AAG TGG GAT CAG AAG GGT ATG   211
 M   V   T   G   G   M   A   S   K   W   D   Q   K   G   M

GAC ATT GCC TAT GAG GAG GCG GCC TTA GGT TAC AAA GAG GGT GGT   256
 D   I   A   Y   E   E   A   A   L   G   Y   K   E   G   G

GTT CCT ATT GGC GGA TGT CTT ATC AAT AAC AAA GAC GGA AGT GTT   301
 V   P   I   G   G   C   L   I   N   N   K   D   G   S   V

CTC GGT CGT GGT CAC AAC ATG AGA TTT CAA AAG GGT TCC GCC ACA   346
 L   G   R   G   H   N   M   R   F   Q   K   G   S   A   T

CTA CAT GGT GAG ATC TCC ACT TTG GAA AAC TGT GGG AGA TTA GAG   391
 L   H   G   E   I   S   T   L   E   N   C   G   R   L   E

GGC AAA GTG TAC AAA GAT ACC ACT TTG TAT ACG ACG CTG TCT CCA   436
 G   K   V   Y   K   D   T   T   L   Y   T   T   L   S   P

TGC GAC ATG TGT ACA GGT GCC ATC ATC ATG TAT GGT ATT CCA CGC   481
 C   D   M   C   T   G   A   I   I   M   Y   G   I   P   R

TGT GTT GTC GGT GAG AAC GTT AAT TTC AAA AGT AAG GGC GAG AAA   526
 C   V   V   G   E   N   V   N   F   K   S   K   G   E   K

TAT TTA CAA ACT AGA GGT CAC GAG GTT GTT GTT GTT GAC GAT GAG   571
 Y   L   Q   T   R   G   H   E   V   V   V   V   D   D   E

AGG TGT AAA AAG ATC ATG AAA CAA TTT ATC GAT GAA AGA CCT CAG   616
 R   C   K   K   I   M   K   Q   F   I   D   E   R   P   Q

GAT TGG TTT GAA GAT ATT GGT GAG TAG                            641
 D   W   F   E   D   I   G   E  STOP
```

EXPRESSION OF DNA SEQUENCES ENCODING A THERMALLY STABLE CYTOSINE DEAMINASE FROM SACCHAROMYCES

CROSS REFERENCE TO RELATED APPLICATION

This is a continuation-in-part of U.S. patent application Ser. No. 365,020, filed 9 June 1989, abandoned which is incorporated herein by reference.

TECHNICAL FIELD

The present invention relates generally to the enzyme cytosine deaminase. More specifically, the present invention relates to the purification and recombinant production of a thermally stable cytosine deaminase derived from *Saccharomyces cerevisiae*.

BACKGROUND OF THE INVENTION

Cytosine deaminase (CDase, EC 3.5.4.1) catalyzes the hydrolysis of cytosine to uracil by the following reaction.

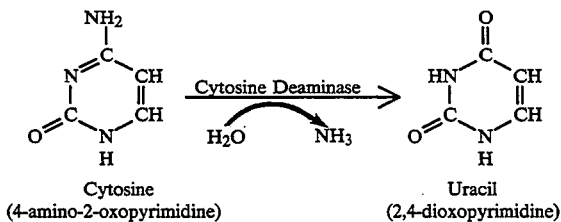

Cytosine (4-amino-2-oxopyrimidine) → Uracil (2,4-dioxopyrimidine)

The enzyme, which plays an important role in microbial pyrimidine metabolism (O'Donovan and Neuhard, 1970), has been isolated from several different microorganisms, but does not appear to be present in mammalian cells (Nishiyama et al., 1985).

The physical properties of CDase from various organisms have been shown to differ significantly in terms of molecular weight, stability, and subunit composition. For example, CDase from *Salmonella typhimurium* has been purified to homogeneity (by SDS-PAGE) and is composed of 4 subunits of 54 kilodaltons (kDa) each (West et al., 1982) while the enzyme from *Escherichia coli* has a molecular weight of 200 kDa and is composed of 35 and 46 kDa subunits (Katsuragi et al., 1986). Both of these enzymes are highly thermostable, and maintain high activity at 55° C.

Bakers' yeast (*Saccharomyces cerevisiae*) has also been used as a source for CDase. CDase previously obtained therefrom has a molecular weight of 34 kDa as determined by gel filtration (Ipata et al., 1971, 1978) and 32–33 kDa as determined by SDS-PAGE and amino acid analysis (Yergatian et al., 1977). The CDase enzyme that has been previously isolated from bakers' yeast therefore appears to be a monomeric protein.

Solutions of previously isolated bakers' yeast CDase maintain activity for at least 48 hr when stored at 4° C. between pH 5–9 (Ipata et al., 1971, 1978). However, at 37° C., a crude preparation of bakers' yeast CDase has been shown to lose half of its activity in 1 hr (Kream and Chargaff, 1952), and a purified forth of the enzyme has a half-life of 30 min (Katsuragi, 1988). The half-life at 37° C. can be increased to 28 days by immobilizing the enzyme onto epoxy-acrylic beads (Katsuragi et al., 1987). Thus, the thermal instability of CDase from bakers' yeast, along with its low molecular weight, distinguish it from the bacterial enzymes described earlier.

CDase has been used therapeutically for the conversion of the prodrug 5-fluorocytosine (5-FC) to the anticancer drug 5-fluorouracil (5-FU) (Katsuragi et al., 1987; Nishiyama et al., 1985; Sakai et al., 1985; Senter et al., 1987). However, bacterial sources of CDase are impractical for such use, requiring large-scale cultivation in order to obtain adequate activity (Sakai et al., 1985). Additionally, microbial extracts can cause undesirable side effects in recipients thereof.

Yeast can be used as a source of CDase to overcome these problems. However, the thermal instability of the previous yeast-derived product requires that the enzyme be immobilized prior to its use (Katsuragi et al., 1987). Thus, the isolation and purification of a thermally stable yeast CDase provides an improved enzyme for use in anticancer therapy. Similarly, cloning the gene for thermally stable CDase from yeast permits the introduction of defined alterations or additions to the gene itself, sequences controlling its expression, and gene fusions created between the gene and other molecules. Such novel constructs increase the efficiency or usefulness of the enzyme in anticancer therapy.

SUMMARY OF THE INVENTION

The present invention is based on the unexpected discovery of a thermally stable CDase from bakers' yeast. Amino acid sequence analysis for this enzyme reveals no significant homology with known sequences of other proteins.

The present invention is directed to an isolated nucleotide sequence encoding a themally stable CDase or a protein functionally equivalent thereto, and to recombinant expression vectors comprising and effective in expressing this sequence, host cells transformed thereby, and methods for producing recombinantly, themally stable, CDase or its functional equivalent.

The present invention is also directed to isolated, themally stable CDase, or a protein functionally equivalent thereto. In a particularly preferred embodiment, the CDase is isolated from *Saccharomyces cerevisiae*.

Additional aspects, benefits and uses of the present invention will readily occur to those of ordinary skill in the art in view of the disclosure herein.

BRIEF DESCRIPTION OF THE FIGURES

In the drawings which constitute a portion of this disclosure:

FIG. 6 depicts the partial amino acid sequence of CDase. Peptides obtained from cleavage with CNBr (M-series), endoproteinase Glu-C (E-series), endoproteinase Lys-C (K-series) and endoproteinase Asp-N (D-series) are indicated.

FIG. 7 shows the nucleotide sequences of primers CDA4R1 and CDASAS, the corresponding amino acid sequences, and the relative positions of these primers in the CDase amino acid sequence. CDA4R1 is oriented 5' to 3' on the sense strand while CDASAS is oriented 5' to 3' on the antisense strand.

FIG. 8 depicts the nucleotide sequence of DNA derived from genomic clones encoding CDase.

FIG. 9 depicts the open reading frames (ORFs) found in the genomic sequence of CDase.

FIG. 10 shows the nucleotide sequence and corresponding amino acid sequence of ORF 2. Additional amino acids, predicted from the nucleotide sequence but not detected by peptide sequencing, are highlighted in boldface type, and the START and STOP codons are boxed.

DETAILED DESCRIPTION

Figure 1:
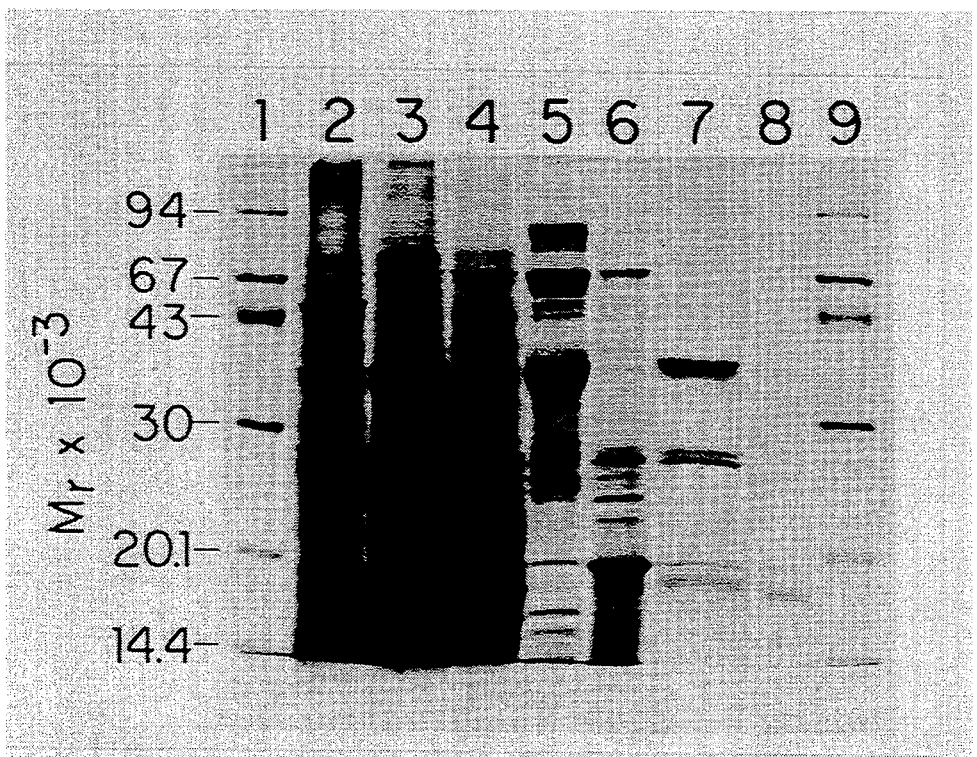
FIG. 1 shows SDS-PAGE analysis of CDase (14% polyacrylamide under non-reducing conditions). The substances depicted in each lane are as follows. Lanes 1 and 9, marker proteins; lane 2, autolysis supernatant from step 1 of Example 1; lane 3, product after $(NH_4)_2SO_4$ precipitation (70%) of Step 2 of Example 1; lane 4, product after $(NH_4)_2SO_4$ precipitation (50–73%) of Step 2 of Example 1; lane 5, product derived after Q-Sepharose chromatography of Step 3 of Example 1; lane 6, product after G-75 column of step 4 of Example 1; lane 7, product after octyl-Sepharose purification of Step 5 of Example 1; lane 8, final product obtained after second G-75 column of Step 6 of Example 1.

The practice of the present invention will employ, unless otherwise indicated, conventional techniques of protein chemistry, molecular biology, microbiology and recombinant DNA technology, which are within the skill of the art. Such techniques are explained fully in the literature. See, e.g., Scopes, R. K., *Protein Purification Principles and Practice*, 2nd ed. (Springer-Verlag 1987); *Methods in Enzymology* (S. Colowick and N. Kaplan eds., Academic Press, Inc.); Maniatis, Fritsch & Sambrook, *Molecular Cloning: A Laboratory Manual*, Second Edition (1989); *Oligonucleotide Synthesis* (M. J. Gait ed. 1984).

A. Definitions

In describing the present invention, the following terms will be employed, and as used herein are intended to be defined as indicated below.

"Thermally stable cytosine deaminase" refers to a CDase that remains at least 50% active in the free, nonimmobilized state, for more than 12 hours at 37° C., preferably for more than i day at 37° C., and most preferably for more than 3 days at 37° C., as determined by monitoring the conversion of 5FC to 5FU in the presence of the isolated enzyme by the assay explained more fully below.

An amino acid sequence or protein is "substantially homologous" to another amino acid sequence or protein when at least about 50%, preferably at least about 85%, and most preferably at least about 90–95%, of the amino acids match over a defined length of the molecule. Additionally, the amino acid variations can include substitutions, deletions or additions.

The term "functionally equivalent" intends that the amino acid sequence or protein defines a chain that will produce a themally stable enzyme, as described above, capable of converting 5-FC to 5-FU as described in the examples. A protein that is functionally equivalent to themally stable CDase need not possess the exact or entire amino acid sequence depicted in the figures herein. Rather, the protein can consist of a biologically active fragment thereof, the activity defined as above. Additionally, the protein can include additions, deletions or substitutions to the depicted sequences, so long as the protein remains biologically active.

A "purified protein" is one substantially free of other materials. For example, protein A is substantially free of B where B is a mixture of other cellular components and proteins, and when at least about 50% by weight of the total A+B present, more preferably at least 75%, and most preferably 90–95% or even 99% by weight, present is A. "Purified" does not, however, refer to the method by which the protein is derived. Thus, a purified protein can be one produced by recombinant techniques, synthetically produced, or isolated directly from an organism in which the protein is found in nature.

The terms "polypeptide" and "protein" are used in their broadest sense, i.e., any polymer of amino acids (dipeptide or greater) linked through peptide bonds. Thus, the terms include oligopeptides, protein fragments, analogs, muteins, fusion proteins and the like. The terms include-native and recombinant proteins.

"Recombinant" proteins or polypeptides refer to proteins expressed from a recombinant nucleotide sequence; i.e., produced from cells transformed by an exogenous DNA construct encoding the desired polypeptide.

The term "recombinant" as used herein to characterize the nucleotide sequence encoding CDase describes nucleic acid of genomic, cDNA, semisynthetic, or synthetic origin which, by virtue of its origin or manipulation is either a nucleotide sequence not occurring in nature or a nucleotide sequence linked to nucleic acids other than that to which it is linked in nature.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about the replication and/or expression of the attached segment. An "expression vector" refers to a vector capable of autonomous replication or integration and contains control sequences which direct the transcription and translation of the desired nucleotide sequence in an appropriate host.

A "coding sequence" is a polynucleotide sequence which is transcribed and/or translated into a polypeptide.

A "promoter sequence" is a DNA regulatory region capable of binding RNA polymerase and initiating transcription of a downstream (i.e., in the 3' direction) coding sequence.

A coding sequence is "under the control" of the promoter sequence in a cell when transcription of the coding sequence results from the binding of RNA polymerase to the promoter sequence; translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence.

"Control sequences" refer to those sequences that control the transcription and/or translation of the coding sequence(s); these may include, but are not limited to, promoter sequences, transcriptional initiation and termination sequences, and translational initiation and termination sequences. In addition, "control sequences" refer to sequences which control the processing of the polypeptide encoded within the coding sequence; these may include, but are not limited to, sequences controlling secretion, protease cleavage, and glycosylation of the polypeptide.

A "signal sequence" can be included before the coding sequence. This sequence encodes a signal peptide, N-terminal to the polypeptide, that communicates to the host cell to direct the polypeptide to the cell surface or secrete the polypeptide into the media. This signal peptide is clipped off by the host cell before the protein leaves the cell. Signal sequences can be found associated with a variety of proteins native to procaryotes and eucaryotes. For instance, alpha-factor, a native yeast protein, is secreted from yeast, and its signal sequence can be attached to heterologous proteins to be secreted into the media (see U.S. Pat. No. 4,546,082). Further, the alpha-factor and its analogs have been found to secrete heterologous proteins from a variety of yeast, such as Saccharomyces and Kluyveromyces (see, e.g., EPO Pub. No. 0 301 669, publication date 1 February 1989).

"Transformation" is the insertion of an exogenous polynucleotide into a host cell. The exogenous polynucleotide may be maintained as a plasmid, or alternatively, may be integrated within the host genome.

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation. Thus, the terms denote progeny of the parental cell which are sufficiently similar to the parent to be characterized by the relevant property, for example, the substitution of a native gens encoding an essential enzyme with a cloned gene linked to a structural gene encoding a desired gene product.

A "therapeutically effective amount" of CDase is an amount that, when administered with a substrate upon which CDase acts, is sufficient to convert the substrate to an active cytotoxic agent which can in turn inhibit tumor cell growth.

B. General Methods

The present invention is directed to a CDase isolated from yeast that exhibits thermal stability. This CDase has properties that distinguish it from the previously isolated CDase enzymes from yeast. The molecular weight of the newly isolated yeast CDase is approximately 32 kDa, as determined by gel filtration chromatography. SDS-PAGE shows a major band at 17 kDa, indicating that the present CDase consists of a dimer, with each subunit having a molecular weight of approximately 17 kDa. In addition, while previously isolated yeast CDase enzymes have been shown to be highly thermolabile at 37° C., the purified enzyme of the instant invention is stable at this temperature. Furthermore, the amino acid sequence of this new CDase shows no significant sequence homology with other known sequenced proteins. Cloning and expression of the gens encoding this unique CDase yields a coding sequence of approximately 474 base pairs in length, specifying a protein of 158 amino acids with a predicted molecular weight of about 17,506 daltons. Thermally stable CDase can be isolated from yeast, including members of the ascosporogenous, basidiosporogenous, and imperfect yeasts. Preferably, CDase is isolated from members of the Saccharomycetoideae family, with Saccharomyces sp. being preferred and *Saccharomyces cerevisiae* (bakers' yeast) being particularly preferred. Fleishmann's Compressed Yeast has been found to be an excellent source of themally stable CDase and is readily available commercially from bakeries and grocery stores.

The current method of purifying CDase differs from reported methods (see, e.g., Katsuragi et al., 1987; Katsuragi et al., 1986; Ipata et al., 1978; Ipata et al., 1971) as well as from that of Katsuragi, 1988. Specifically, the method employs different purification steps, including an additional gel permeation column purification between anion-exchange and hydrophobic chromatography steps (described below), as well as different conditions for purification including difference buffers, pHs and buffer constituents, such as EDTA and DTT. Furthermore, previous methods do not render a thermally stable enzyme.

The first step in the purification of thermally stable CDase from yeast involves the disruption of yeast cells to render an autolysate containing CDase. Autolysis can be achieved using any of several methods known in the art. For example, yeast cells can be plasmolyzed with toluene according to the method of Kunitz (1947). Particularly useful is the exposure of yeast to an organic solvent such as ethyl acetate followed by the addition of a buffer to maintain the solution at approximately pH 7. Suitable buffers include potassium phosphate buffer, phosphate buffered saline, Tris buffer, as well as several others well known in the art. The buffer preferably contains ammonium sulfate at concentrations ranging from i to 25%, preferably 15%, as well as EDTA and dithiothreitol (DTT) to stabilize CDase. Alternatively, EDTA and DTT can be eliminated from this and subsequent buffers. The concentration of EDTA, when present, ranges from 0.1 mM to 10 mM, with 5 mM being preferable, while DTT can be present at concentrations from 0.01 mM to 10 mM, preferably 0.1 mM. This mixture is stirred for several days, and the pH maintained at about 7. Cell debris can be removed by centrifugation.

Following autolysis, total protein is precipitated from the autolysate using ammonium sulfate. Ammonium sulfate is added at concentrations sufficient to yield a higher CDase to protein ratio. For example, ammonium sulfate can first be added to reach between 60–80% saturation, preferably 70% saturation. EDTA is preferably included in the reaction mixture at a concentration of between 1–3 g/l, more preferably 1.5–2.0 g/l, the reaction allowed to proceed for several hours, and the precipitate collected after centrifugation. The pellet is dissolved in a suitable buffer, such as PBS, at approximately pH 7.0, the buffer preferably containing EDTA and DTT, as above, and the solution dialyzed against the same buffer. The dialysate can be treated a second time with ammonium sulfate to reach a concentration of about 50%, with EDTA being present as above. The precipitate is again collected by centrifugation and ammonium sulfate added to the supernatant to reach about 73% saturation. The precipitate is collected and dissolved in a suitable buffer of about pH 6.5–8.5, preferably a Tris buffer at pH 8.0 containing DTT at the concentration described above. The reconstituted precipitate is then dialyzed against this buffer for several hours. CDase from the dialysate can be further purified by anion-exchange chromatography using, for example, a cross-linked agarose or cellulose packing material- Particularly suitable are anion exchangers such as Q-Sepharose and DEAE-Sepharose, available from Pharmacia. Suitable equilibration buffers include, for example, Tris or phosphate buffers, with elution being accomplished using a linear gradient. Particularly suitable is the use of 20 mM Tris containing 0.1 mM DTT at pH 8.0, with a linear gradient of 0–0.3 M KCl in this buffer.

Following anion exchange chromatography, the fractions containing CDase activity (assessed as described below) are pooled and concentrated by ultrafiltration using, for example, a filter with a molecular weight cutoff of about 30,000 daltons (Da) or less.

Next, the CDase-containing solution is run on a gel permeation column. Particularly useful are cross-linked dextran, agarose, or dextran/bisacrylamide gels with Sephadex G-75, G-100 or Sephacryl S-300 being preferred. The eluant can be any conventional buffer, well known in the art, at about pH 7, with PBS containing DTT as previously described being preferred. Fractions containing CDase activity are pooled and dialyzed against a buffer such as potassium phosphate. Preferably, the buffer contains about 1–2 M ammonium sulfate, and EDTA and DTT as described above with respect to the autolysate buffer. A second gel permeation column can be run if desired and the active fractions concentrated by ultra-filtration using a filter with a molecular weight cutoff of, for example, 5000 Da.

Next, the CDase-containing material can be applied to a column that separates substances based on hydrophobicity and eluted using, for example, a reverse gradient of ammonium sulfate in potassium phosphate buffer. Fractions with CDase activity are combined and concentrated by ultrafiltration, using a filter with a molecular weight cutoff of 5000 Da. The concentrate can be stored frozen for further use. However, if a second gel permeation column was not carried out and/or if specific activity of the CDase is low, another gel permeation column, as described above, can be run. CDase thus purified is themally stable and can therefore be stored frozen or lyophilized in the free form.

The activity of the CDase can be monitored during purification by several methods known in the art. For example, conversion of cytosine to uracil, or derivatives thereof, in the presence of CDase, can be monitored by a direct spectrophotometric assay from the fall in absorbance at 286 nm following the conversion. (See, e.g., Ipata and Cercignani, 1978.) Alternatively, activity can be determined by monitoring conversion of 5FC to 5FU spectrophotometrically as described by Nishiyama et al., 1985, and incorporated herein by reference.

Thermally stable CDase purified in this manner has been sequenced as described in the experimental section and the partial amino acid sequence can be seen in FIG. 6. The sequence shows no substantial homology with other known sequenced proteins. Based on this information, thermally stable CDase can be produced recombinantly. For example, DNA sequences encoding CDase can be prepared synthetically, based on the amino acid sequence obtained, using appropriate codohs. In general, one will select preferred codons for the intended host used for expression of CDase. The complete sequence is assembled from overlapping oligonucleotides prepared by standard methods. See, e.g., Edge (1981) *Nature* 292:756; Nambair et al. (1984) *Science* 223:1299; Jay et al. (1984) *J. Biol. Chem.* 259:6311.

Alternatively, recombinant, themally stable CDase can be prepared as follows. Oligonucleotide probes containing codone for a portion of the determined amino acid sequence can be prepared and used to screen genomic or cDNA libraries for the gens encoding CDase. Basic strategies for preparing oligonucleotide probes and DNA libraries, as well as their screening by nucleic acid hybridization, are well known to those of ordinary skill in the art. See, e.g., *Oligonucleotide Synthesis*, supra; T. Maniatie et al., supra. Once a clone from the screened library has been identified by positive hybridization, restriction enzyme analysis and DNA sequencing can be done to confirm that the particular library insert contains the gene encoding CDase. Additionally, the polymerase chain reaction (PCR) can be used to amplify and subsequently detect the nucleotide sequence coding for CDase. This method is described in Saiki et al. (1986) and in U.S. Pat. Nos. 4,683,195 and 4,683,202, the disclosures of which are incorporated herein by reference. Analysis of the nucleotide sequence of the PCR-amplified products can be accomplished by direct sequence analysis as described by Saiki et al. (1988). Alternatively, the amplified target sequence(s) can be cloned prior to sequence analysis. A method for the direct cloning and sequence analysis of enzymatically amplified genomic segments has been described by Scharf et al. (1986). In the method, the primers used in the PCR technique are modified near their 5'-ends to produce convenient restriction sites for cloning directly into, for example, an M13 sequencing vector. After amplification, the PCR products are cleaved with the appropriate restriction enzymes. The restriction fragments are ligated into the M13 vector, and transformed into, for example, a JM 103 host, plated out, and the resulting plaques are screened by hybridization with a labeled oligonucleotide probe. Other methods for cloning and sequence analysis are known in the art.

In a particularly preferred method for use with the present invention, two oligonucleotide primers were synthesized using the partial amino acid sequence and the codon usage patterns from *S. cerevisiae* (Guthrie and Abelson, 1982) as a guide in designing "guessmer" sequences of DNA sequence. These primers were used for PCRs in which cloned yeast genomic library DNA was present as template. The oligonucleotides were synthesized from regions of CDase in which the amino acids show marked codon usage bias and/or few degeneracies. The first primer, CDA4R1, was a 42-mer containing 33 nucleotides corresponding to an amino terminus amino acid sequence, while the second, CDA5AS, contained nucleotides complementary to sequence located near the carboxy-terminus of the protein. The sequence of these oligonucleotides is shown in FIG. 7. Two genomic libraries were used as template DNA in PCR reactions and both were found to yield a single specific fragment approximately 350 base pairs in length, the size predicted from the corresponding amino acid sequence available. The PCR primers were engineered with EcoRI restriction sites at their 5' ends to facilitate cloning of fragments generated by PCR. The 350 base pair PCR derived fragment was purified by gel electrophoresis and subcloned into an appropriate vector for DNA sequencing.

The PCR-derived fragment was also used as a CDase specific probe for screening yeast libraries by colony filter hybridization techniques. Initial attempts to use the guessmer oligonucleotides as probes failed because of a low signal:noise ratio after hybridization. All potential clones were picked and rescreened twice to verify the positive hybridization signal. Plasmids were purified from individual clones and restriction mapped by digestion with a series of restriction enzymes both alone and in various multiple digestion reactions.

Both the cloned PCR fragments and the genomic clones encoding CDase were subjected to DNA sequence analysis. Variations in the reaction conditions permitted analysis of sequences directly adjacent to the primer to several hundred base pairs away. The DNA sequence obtained is shown in Figure 8. As can be seen, the sequences are 93% homologous having 23 mismatches and 330 matches. ORFs found within this sequence are shown in FIG. 9. FIG. 10 shows the nucleotide sequence and deduced amino acid sequence of ORF 2, confirming the previously determined amino acid sequence and predicting the addition of only a few amino acids to either end of the partial sequence obtained by analysis of the purified protein.

The DNA sequence data was subsequently used to design new PCR primers for generating amplified DNA cassettes coding for CDase- Such cassettes can be used in genetic constructs designed to produce high levels of gene expression in either procaryotic or eucaryotic cells, and to generate gens fusions between CDase and other molecules of biological interest including but not limited to immunoglobulin molecules targeted against cancer antigens.

The CDase coding sequence can be cloned into any suitable vector or replicon, well known in the art. Examples of recombinant DNA vectors for cloning and host cells which they can transform, in parentheses, include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-E. coli gram-negative bacteria), pHV14 (*E. coli* and *Bacillus subtilis*), pBD9 (Bacillus), pIJ61 (Streptomyces), pUC6 (Streptomyces), YIp5 (Saccharomvces), YCp19 (Saccharomvces) and bovine papilloma virus (mammalian cells).

The coding sequence for the CDase protein can be placed under the control of a promoter, ribosome binding site (for bacterial expression) and, optionally, an operator (collectively referred to herein as "control" elements), so that the DNA sequence encoding the protein is transcribed into RNA in the host cell transformed by a vector containing this expression construction. The coding sequence may or may not contain a signal peptide or leader sequence. Leader sequences can be removed by the bacterial host in post-translational processing. See, e.g., U.S. Pat. Nos. 4,431,739; 4,425,437; 4,338,397.

In addition to control sequences, it can be desirable to add regulatory sequences that allow for regulation of the expression CDase sequences relative to the growth of the host cell. Regulatory sequences are known to those of skill in the art, and examples include those that cause the expression of a gene to be turned on or off in response to a chemical or physical stimulus, including the presence of a regulatory compound. Other types of regulatory elements can also be present in the vector, for example, enhancer sequences.

An expression vector is constructed so that the CDase coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding CDase can be desirable to achieve this end. For example, in some cases it may be necessary to modify the sequence so that it can be attached to the control sequences with the appropriate orientation; i.e., to maintain the reading frame. The control sequences and other regulatory sequences can be ligated to the coding sequence prior to insertion into a vector, such as the cloning vectors described above. Alternatively, the coding sequence can be cloned directly into an expression vector that already contains the control sequences and an appropriate restriction site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. Mammalian expression vectors are also known.

Depending on the expression system and host selected, CDase is produced by growing host cells transformed by an expression vector described above under conditions whereby the CDase is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

Figure 11:
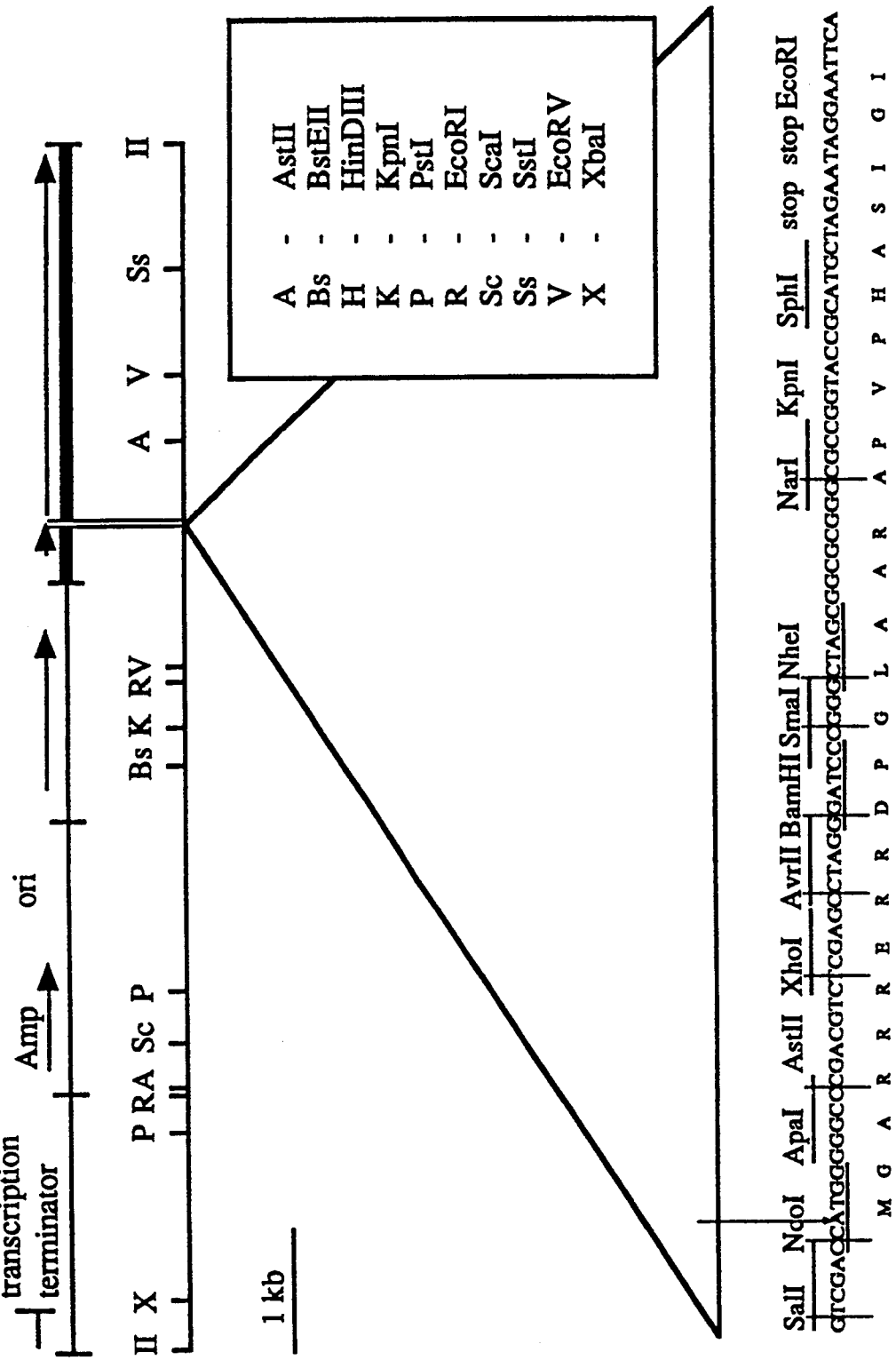
FIG. 11 illustrates the plasmid expression vector "fusionator" containing the CDase gene.

An example of one construct for controlled induction of CDase sequences in yeast involves the insertion of the CDase cassette into a yeast vector called the "fusionator". This vector is available from the Department of Genetics, University of Washington, Seattle, Wash., and from NIH. Such a construct is depicted in FIG. 11. In this construct, CDase is inserted into a polylinker which places its expression under the control of the highly expressed and stringently regulated GAL10 promoter from yeast (Johnston, M. 1987). The GAL10 promoter responds to galactose, inducing high level expression of the gens under its control. This vector can also be used to create a CDase-lacZ gene fusion by the appropriate alterations in DNA sequence. The fusion protein generated may facilitate quantitation of induction, purification, and biochemical analysis. These constructs can be transformed into a suitable yeast strain, such as that described by Hovland, et al., (1989). This yeast strain includes a number of mutations making it desirable for use with a construct such as described above. Specifically, a gal1 mutation is present which results in a deficiency for the enzyme which catalyzes the first step of galactose utilization, thus preventing depletion of the inducer (galactose) in the media. A reg1-501 mutation is also present which eliminates glucose repression of galactose gene expression and permits the establishment of cultures under conditions optimal for growth and viability. Induction can be easily achieved by addition of galacrose to rich glucose-based media. Finally, several protease deficient mutations are present in the strain, increasing the stability of any heterologous proteins or fragments thereof, produced during growth. Such an expression construct should facilitate isolation and purification of CDase from yeast in amounts previously impossible using the expression levels obtained with the endogenous gene.

Other constructs can be created for use in mammalian cell culture systems. In one preferred embodiment of the invention, the cassette encoding CDase is attached using PCR technology to the secretory signal peptide for oncostatin M (Malik, et al., 1989), and can then be inserted into the mammalian expression vector pH3MPy (Stamenkovic, et al., 1990) which contains appropriate enhancers, promoters, termination, and processing signals for mammalian expression. The construct can be transfected into COS cells, (Aruffo and Seed, 1987) serum-free culture medium collected, and assayed for CDase activity in a system lacking endogenous enzyme activity. Similarly, cDNA constructs for gene fusions between CDase and other molecules of interest can be constructed by standard techniques, transfected into COS cells, and cell extracts or supernatants assayed for the proteins and their activity.

Other gene fusions will also find use in the recombinant production of CDase. For example, a nucleotide sequence encoding for CDase or a functional mutant or fragment thereof, can be fused to cDNA-encoding immunoglobulin molecules targeted against cancer antigens, to create an antibody-enzyme fusion protein. Monoclonal antibodies have been obtained which recognize determinants preferentially expressed on tumor cells (Hellstrom, et al., 1984). Thus, fusion proteins can be created which specifically target select tumor cells. See, e.g., U.S. Pat. No. 4,906,562 and Hellstrom and Hellstrom, 1985. The enzyme can then act directly at the tumor cell site to convert the prodrug 5FC into the anticancer agent 5FU. Genomic fusions between genes encoding the enzyme of interest and the antibody targeted to cancer cells eliminates the requirement for chemical conjugation of the two proteins. Similarly, cDNA constructs between two molecules of interest could increase the flexibility of such constructs in heterologous expression systems.

In one system, the cDNA for the heavy chain of a cancer antibody is obtained from cell lines producing this antibody. PCR fragments encoding all or parts of this cDNA can then be generated by methods familiar to those skilled in the art. In-frame fusion of the two cassettes can be achieved by standard techniques at several locations, and the resulting fusions tested for production of proteins with the desired biological activity. Co-transfection with a second plasmid carrying the cDNA encoding the light chain portion of the antibody molecule permits isolation of a biologically active antibody fragment fused to an active CDase enzyme. Thus, targeting of the enzyme to the desired location will be achieved.

It is also desirable to produce mutants or analogs of themally stable CDase which are functionally equivalent thereto. Mutants or analogs can be prepared by the deletion of a portion of the sequence encoding CDase, by insertion of a sequence, and/or by substitution of one or more nucleotides within the sequence. Techniques for modifying nucleotide sequences, such as site-directed mutagenesis or PER oligonucleotide mutagenesis, are well known to those skilled in the art. See, e.g., T. Maniatie et al.

CDase of the present invention is also produced by chemical synthesis such as solid phase peptide synthesis, using known amino acid sequences or amino acid sequences derived from the DNA sequence of the gene of interest. Such methods are known to those skilled in the art.

Thermally stable CDase can be used as a chemotherapeutic agent. Specifically, this enzyme can be used in vivo to convert the prodrug 5FC into the anticancer agent 5FU. Thus, CDase can be coadministered with 5FC such as by surgically placing CDase at or near the tumorous site and administering 5FC orally, as described by Katsuragi et al., 1987, the disclosure of which is incorporated herein by reference. Alternatively, the enzyme can be delivered to the tumor site by targeting delivery of a CDase/antibody complex to tumors using antibodies specific for those tumors. This complex can be produced by chemical methods, or genetically, by constructing gens fusions between the appropriate immunoglobulin gens and the CDase gene, as described above.

Below are examples of specific embodiments for carrying out the present invention. The examples are offered for illustrative purposes only, and are not intended to limit the scope of the present invention in any way.

EXAMPLE 1

Enzyme Purification, Activity Determination and Characterization of CDase

CDase was purified from Fleishmann's compressed bakers' yeast using the following method. All steps in the purification were carried out at 4° C. The enzyme activity was determined with 5' fluorocytosine (5FC) at 3 mM in phosphate buffered saline (PBS) at 37° C. (Nishiyama, et al., 1985), the disclosure of which is incorporated herein by reference in its entirety. Solutions of the enzyme were added, and the course of reaction was monitored spectrophotometrically on aliquots that were quenched with 0.1 N HCl. Absorbance ratios of 255/290 were used to measure the amount of 5-fluorouracil (5FU) formed. One unit of enzyme activity is defined as 1 umol 5FU formed per minute at 37° C. Protein concentration was measured using the BCA assay available from Pierce (Rockford, IL). SDS-PAGE was used to monitor the protein composition after each purification step.

Step 1. Preparation of Yeast Autolysate

Bakers' yeast (2.25 kg) was mixed with ethyl acetate (225 mL) and stirred for 30 min. To this was added 2.25 L of 50 mM potassium phosphate buffer at pH 7.2 containing 15% ammonium sulfate, 5 mM EDTA and 0.1 mM dithiothreitol (DTT). The mixture was stirred for 3 days and the pH was adjusted daily to pH 7.2 with solid trihydroxymethylaminomethane (Tris). The cell debris was removed by centrifugation at 10,000 rpm for 15 min.

Step 2. Ammonium Sulfate Fractionation

Total protein was precipitated from the supernatant of Step 1 by adding EDTA (1.8 g/L) and ammonium sulfate (371 g/L) thereto so that the final concentration of ammonium sulfate was 70% saturation. The solution was held at 4° C. for about 16 hours, after which the precipitate was collected by centrifugation. The pellet was dissolved in 1.5 L of 50 mM potassium phosphate buffer at pH 7.2 containing 5 mM EDTA and 0.1 mM DTT and dialysis against this buffer was allowed to proceed for about 12 to 16 hours.

EDTA (1.8 g/L) was added to the dialysate, and ammonium sulfate was added to reach 50% saturation (314 g ammonium sulfate/L dialysate). After 1 hr, the precipitate was centrifuged and additional ammonium sulfate was added to the supernatant so that the final ammonium sulfate concentration was 73% saturation. The precipitate was collected, dissolved in 1L of 20 mM Tris buffer at pH 8.0 containing 0.1 mM DTT, and dialyzed extensively with this buffer for about 12 to 16 hours.

Step 3. Artion-Exchange Chromatography

The dialysate from Step 2 was applied to a 4.8×25 cm Q-Sepharose (Pharmacia) column which was equilibrated in 20 mM Tris containing 0.1 mM DTT at pH 8.0. The column was washed, and the enzyme was eluted with a linear gradient of 0–0.3 M KCl in the above buffer. The fractions containing CDase activity were pooled and concentrated to approximately 15 mL by ultrafiltration (Amicon, PM 30 filter).

Step 4. Gel Permeation Chromatography

The CDase containing solution from Step 3 was applied to a G-75 Sephadex column (2.5×100 cm) and eluted with PBS containing 0.1 mM DTT. The fractions containing CDase activity were pooled and then dialyzed against 4L of a 100 mM potassium phosphate buffer containing 1.8M ammonium sulfate, 5 mM EDTA and 0.1 mM DTT at pH 7.0.

Step 5. Hydrophobic Interaction Chromatography

The material from Step 4 was applied to a 2.5×15 cm octyl-Sepharose (Pharmacia) column which was equilibrated with 100 mM potassium phosphate containing 1.8M ammonium sulfate, 5 mM EDTA and 0.1 mM DTT at pH 7.0. The column was washed with this buffer, and the enzyme was eluted with a linear gradient of 1.8–0M ammonium sulfate in the above phosphate buffer. The fractions containing CDase activity were combined and concentrated by ultrafiltration (Amicon, YM5 filter).

Step 6. Gel Permeation Chromatography

A final gel filtration of the material from Step 5 on G-75 Sephadex using PBS as eluant was performed as described in Step 4. The purified enzyme was concentrated by ultrafiltration and stored at −70° C.

The step by step results of the purification can be seen in Table 1. SDS-PAGE profiles, used to monitor the protein composition after each purification step, can be seen in FIG. 1. The final enzyme preparation consisted of a major band at approximately 17 kDa and a minor band at approximately 19 kDa.

TABLE 1

| Purification of CDase from 2.25 kg of Bakers' Yeast | | | | |
|---|---|---|---|---|
| Step | Total Protein (mg)[1] | Total Activity (U)[2] | Specific Activity (U/mg) | Fold Purification |
| Cell-free extract | 120,000 | 1750 | 0.014 | 1 |
| (NH$_4$)$_2$SO$_4$ | 36,000 | 1274 | 0.035 | 2.5 |
| Q-Sepharose | 4,200 | 685 | 0.16 | 11.4 |
| G-75 Sephadex | 184 | 648 | 3.5 | 250 |
| Octyl-Sepharose | 20 | 495 | 25 | 1,800 |
| G-75-Sephadex | 6 | 394 | 67 | 4,800 |

[1]Protein concentration determined using BCA (Pierce).
[2]One unit of enzyme activity is defined as 1 umol 5FU formed per minute at 37° C.

Figure 2A:
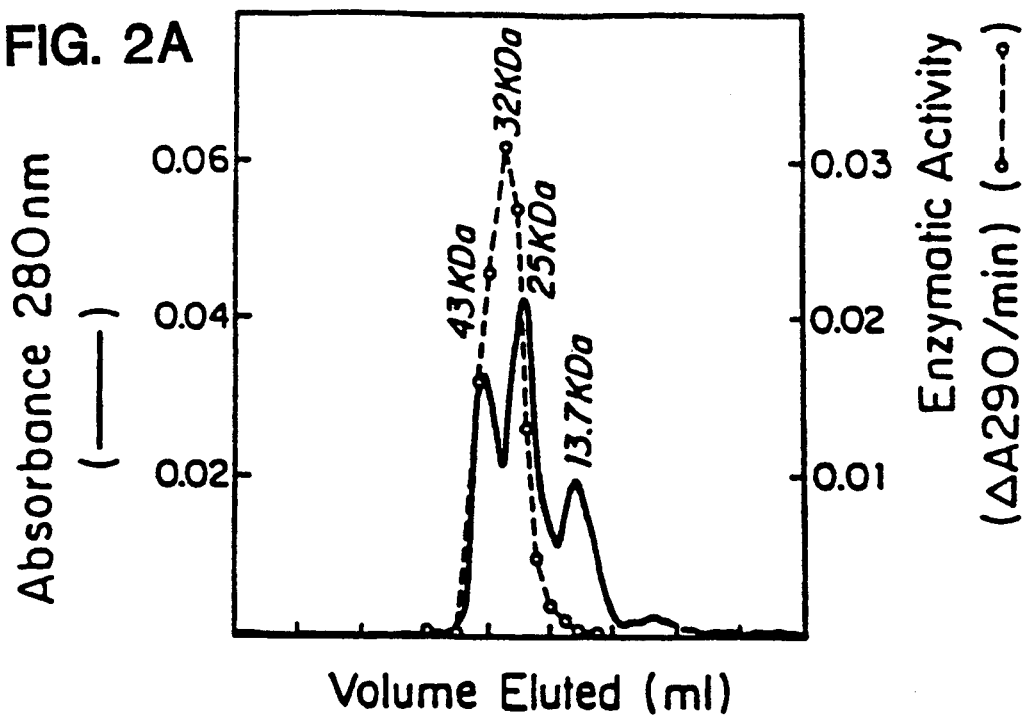
FIG. 2 depicts the elution profile of CDase from a G-S0 Sephadex column (1.5×100 cm). (A) 27 U of purified CDase was mixed with ribonuclease A (2 mg), ovalbumin (2 mg) and chymotrypsinogen A (1 mg) and eluted with PBS. Fractions were monitored at 280 nm to determine total protein content, and at 290 nm using 5FC as a substrate to determine CDase activity. (B) Elution of CDase off the G-50 Sephadex column above without the calibration standards.
Figure 2B:
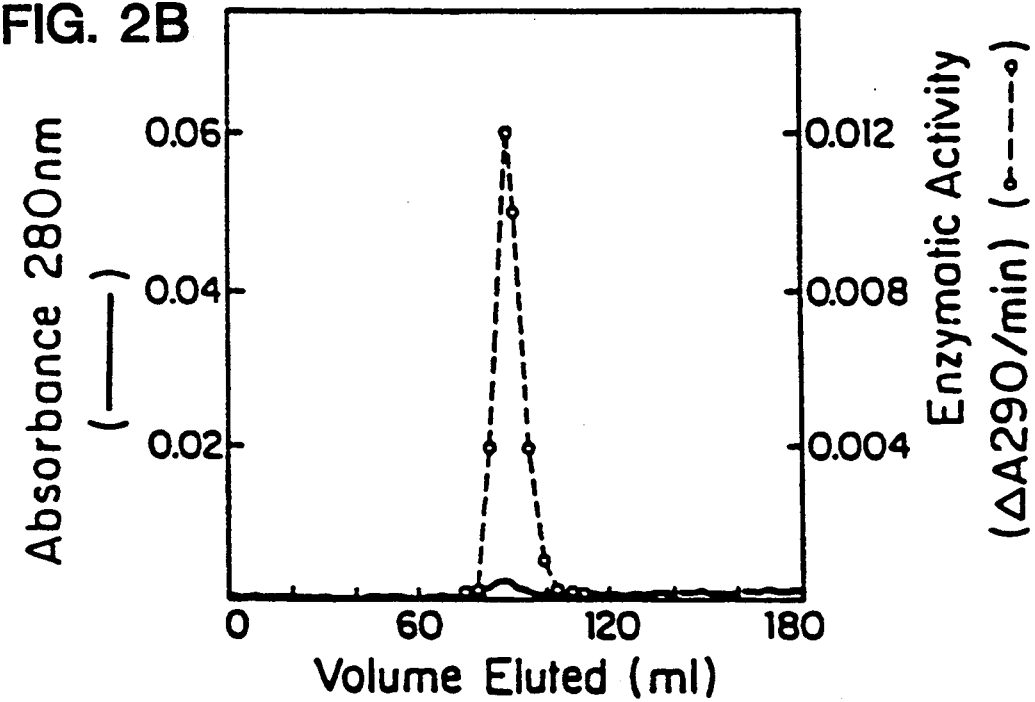

The molecular weight of CDase was determined by applying the purified enzyme to a G-50 Sephadex column along with ribonuclease A (13.7 kDa), chymotrypsinogen A (25 kDa) and ovalbumin (43 kDa). Fractions were monitored at 280 nm to measure total protein, and for CDase activity using 5FC as a substrate. CDase enzyme activity was centered at approximately 32 kDa (FIG. 2A). The enzyme eluted exactly in the same volume when applied to the column without the calibration standards (FIG. 2B).

Figure 3:
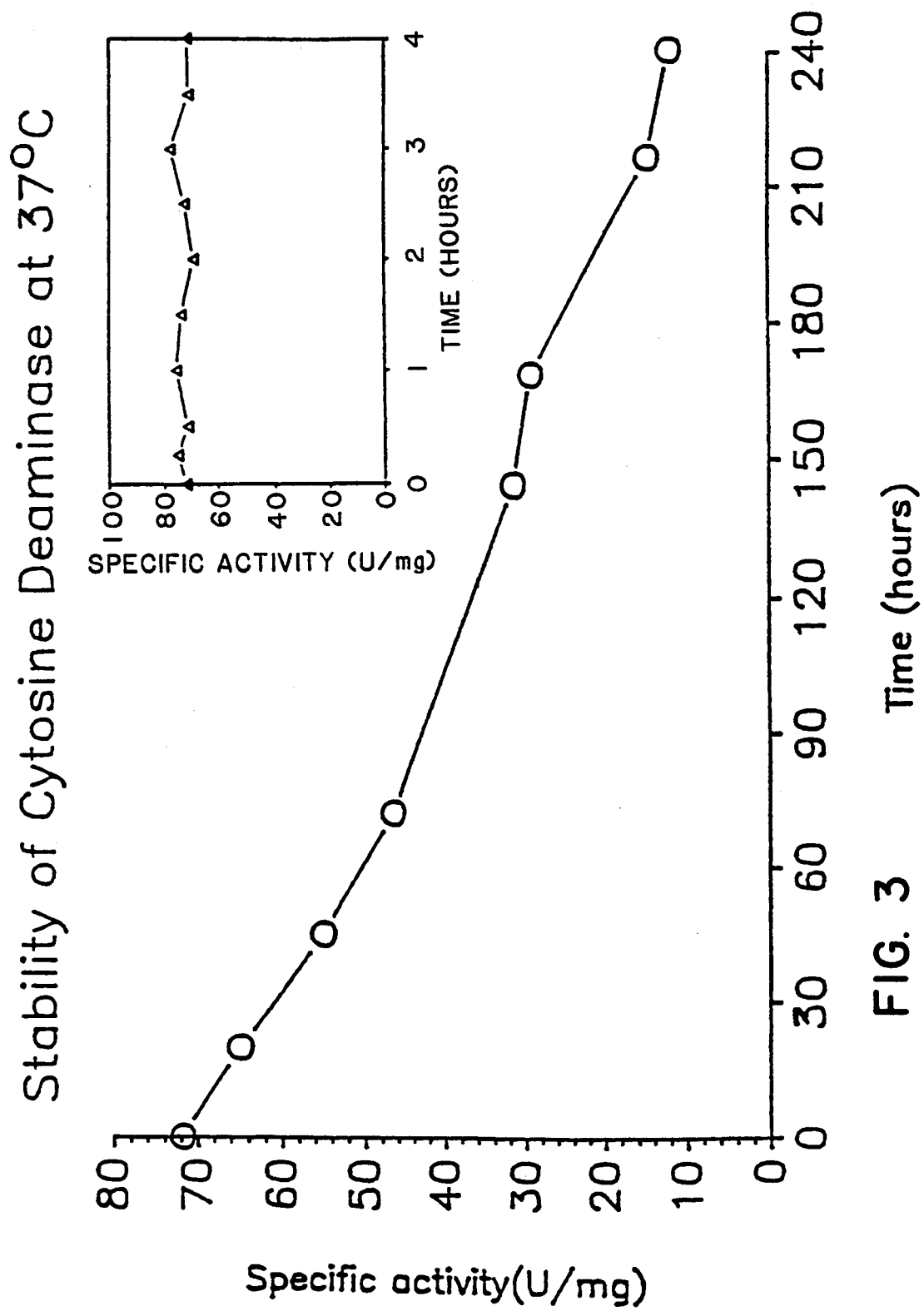
FIG. 3 illustrates the stability of CDase at 37° C. CDase (72 U/mg) in PBS that contained protease-free BSA (1 mg/ml) was incubated at 37° C. in a polypropylene tube. At various intervals, the CDase activity was determined using 10 ul of the enzyme solution.

The stability of the purified CDase at 37° C. in phosphate buffered saline at pH 7.2 was determined using 5FC as a substrate. A slow decrease in enzyme activity was observed after prolonged incubation (FIG. 3). Under these conditions, the enzyme lost half of its activity after 5.2 days. There was no apparent loss of enzymic activity in the first 4 hr of incubation (FIG. 3 inset).

Example 2

Amino Acid Sequence of CDase

The reagents used for sequencing CDase were obtained from Applied Biosystems, Inc. The solvents used for reverse phase HPLC were from Burdick and Jackson. 4-Vinylpyridine was from Aldrich Chemical Co., CNBr was from Kodak, and all other chemicals were reagent grade. Endoproteinase Glu-C from *Staphylococcus aureus* was obtained from Miles Laboratories. Encoproteinase Asp-N from *Pseudomonas fragi* and endoproteinase Lys-C were obtained from Boehringer Mannheim.

Automated sequence analysis was performed on a model 475A amino acid sequencer (ABI) using the RUN470-L or PRO470-L programs. A total of 1.5 mg BioBrene (ABI) was applied and subjected to two or three precycles of Edman degradation prior to sample application. Conversion of the thiazolinone derivatives to phenylthiohydantoin amino acids was carried out with 25% TFA at 61° C. Phenylthiohydantoin amino acid derivatives were separated by reversed phase HPLC on a PTH C18 column (2.1×220 mm, ABI) with a sodium acetate buffer containing 5% (v/v) tetrahydrofuran as starting buffer and acetonitrile containing 500 nM dimethylphenylthiourea (ABI) as limiting buffer on a model 120A PTH analyzer (ABI).

CDase and peptide fragments were purified using reversed phase HPLC on a model 130A separation system (Applied Biosystems, Inc.). Separation was carried out at 40° C. on an RP-300 column (2.1×30 mm; ABI). A linear gradient of 0–60% acetonitrile in 0.1% aqueous trifluoro-acetic acid (TFA) over 2 hr at 0.1 ml/min was used to elute the proteins and peptide fragments. CNBr peptides, endoproteinase Lys-C peptides, endoproteinase Glu-C, and endoproteinase Asp-N peptides, were used for sequence analysis without further purification.

Reaction of CDase with 4-Vinylpyridine.

The CDase from Example 1, Step 6, was modified by the addition of 4-vinylpyridine in the following manner. CDase was reduced with 20 mM dithiothreitol in 0.1 ml of 0.4 M Tris-HCl buffer, pH 8.5, containing 6M guanidine-HCl, 0.1% Na$_2$EDTA, at 50° C. for 2 hr, and then reacted with 100 mM 4-vinylpyridine overnight at room temperature. The reaction mixture was acidified to pH 2.0 with 20% TFA, desalted and purified by reversed phase HPLC as described above.

Figure 5:
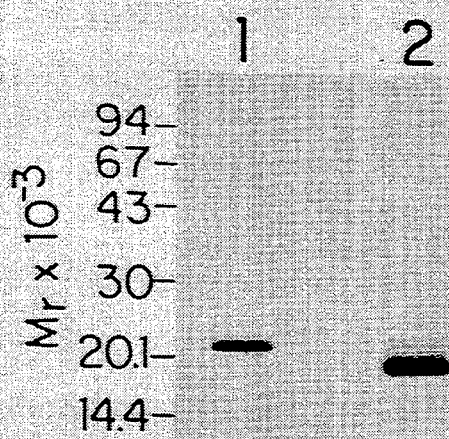
FIG. 5 illustrates SDS-PAGE analysis of CDase after HPLC purification (15% polyacrylamide under reducing conditions). Lane 1, pool A; lane 2, pool B.

HPLC analysis of the resulting product indicated the presence of two distinct peaks (FIG. 4) which were separated and re-analyzed by SDS-PAGE (FIG. 5). The smaller peak (pool A) corresponded to the 19 kDa band in FIG. 1 and the larger peak corresponded to the 17 kDa band.

The amino-terminal amino acid sequence for the protein in pool A (FIG. 4) was obtained by the identification of the amino acid phenylthiohydantoin derivatives up to residue 27. The sequence was found to be identical to the N-terminal sequence of bakers' yeast superoxide dismutase (EC 1.15.1.1, Steinman, 1980). This established the identity of the minor band seen in the gels of purified CDase (FIG. 1, 5).

Figure 4:
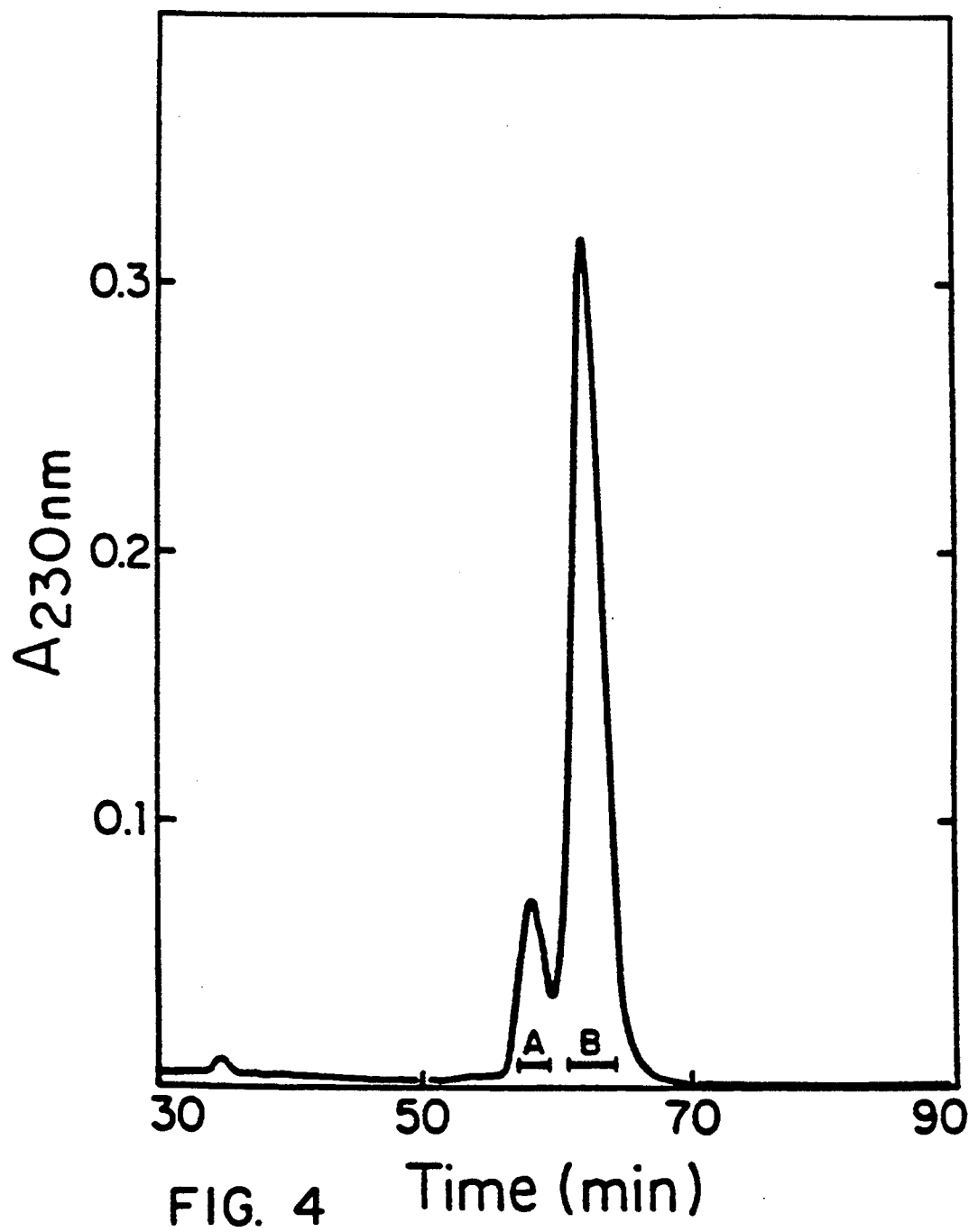
FIG. 4 shows the profile of HPLC-purified CDase. The horizontal bars indicate the fractions that were pooled for amino acid sequence analysis.

No amino acid sequence was obtained from Edman degradation of the large peak in FIG. 4 (pool B), suggesting that the amino terminus of CDase was blocked. The partial amino acid sequence of CDase was therefore obtained by sequencing selected fragments from enzymatic and cyanogen bromide degradation, as described below.

Enzymatic and Chemical Cleavage of CDase

Cleavage of the CDase that was modified with 4-vinylpyridine with endoproteinase Lys-C and endoproteinase Glu-C was done in 40 ul of 0.1M Tris-acetic acid buffer (pH 8.0) at 37° C. for about 12 to 16 hours. The enzyme/substrate ratio was 1:10 (wt/wt), respectively. Endoproteinase Asp-N cleavage was done in a similar manner at an enzyme/substrate ratio of 1:100 at 37° C. for about 12 to 16 hours. The enzymatic digests were acidified with 20% TFA to pH 2.0 and separated by reversed phase HPLC.

Cyanogen bromide (CNBr) was used to cleave CDase at methionyl residues. CDase (2.25 nmol) that was modified with 4-vinylpyridine, was reconstituted in 40 ul of 70% formic acid, and a 200-fold molar excess of CNBr in 70% formic acid was added. The reaction was allowed to proceed at 35° C. for 2 hr, and then for about 12 to 16 hours at room temperature. The digest was diluted with water and vacuum-dried to remove excess CNBr. A solution for reversed phase HPLC analysis was prepared in 1% TFA.

FIG. 6 shows the partial amino acid sequence of CDase based on the fragments obtained from cyanogen bromide cleavage, and proteolytic cleavage using the enzymes, endoproteinase Glu-C, endoproteinase Lys-C and endoproteinase Asp-N. A stretch of 154 amino acids was identified which comprises the bulk of the protein. The numbering of the amino acid residues does not include those amino acids near the amino terminus which have not yet been identified. Comparison of the partial CDase sequence with any other known sequences, including mouse adenosine deaminase (Yeung et al., 1985) and bakers' yeast dCMP deaminase (Mcintosh and Haynes, 1986), did not reveal any substantial homology.

EXAMPLE 3

Cloning and Expression of the CDase Gene

The gene encoding CDase was isolated from laboratory strains of S. cerevisiae (baker's yeast) and expressed in a mammalian cell line using the following method:

Step 1: Generation of CDase Specific Probe using PCR

Two oligonucleotide primers were synthesized on an automated DNA synthesizer using the partial amino acid sequence and the condon usage patterns from S. cerevisiae (Guthrie and Abelson, 1982) as a guide in designing "guessmer" segments of DNA sequence. These oligonucleotides were then used as primers in PCRs with cloned yeast genomic library DNA present as template.

The primers, termed CDA4R1 and CDASAS, were both 42-mers containing 33 nucleotides of sequence corresponding to CDase sense and antisense strands, respectively. The remainder of each oligonucleotide coded for the restriction enzyme site for EcoRI. The sequence of the two primers is shown in FIG. 7.

Both primers were present at either 50 or 100 pmols per reaction. The two genomic libraries used as template DNA in PCR reactions were constructed from yeast genomic DNA by Sau3A partial restriction digestion followed by ligation into the BamHI sites of either the CV13 or YCp50 shuttle vector. These two vectors and the genomic libraries are generally available to those in the field, and were obtained from the Department of Genetics at the University of Washington. Both libraries were obtained already transformed into bacterial hosts. Library DNA was isolated by alkaline lysis plasmid preparations which had been subsequently purified by centrifugation through cesium chloride-ethidium bromide density gradients. PCR reactions were set up using 1 ug of CsCl purified CV13 or YCp50 genomic library DNA from yeast, 50 or 100 pmols of each primer, 1/10 volume of 10x PCR reaction buffer (Stratagene), 16/100 volume of 1.25 mM dNTP's (A, G, T, C), PCR grade distilled water, and 0.5 ul of Taq DNA polymerase (5U/ul, Stratagene), to a final volume of 100 ul. Reactions were performed in sterile microfuge tubes under a 75 ul layer of purified mineral oil to prevent evaporation. PCR reactions were run in a Perkin-Elmer Cetus Thermal Cycler on a 30-cycle program incorporating the following temperature shifts: a step cycle of 94° C. for 30 seconds to denature, 55° C. for 45 seconds to anneal, and 72° C. for 1.5 minutes (90 seconds) to extend.

Aliquots from PCR reactions were analyzed on agarose gels for evidence of the predicted 350 base pair fragment encoding most of CDase. The 350 base pair fragments were then purified by preparative agarose gel electrophoresis followed by solution using the protocol and reagents supplied with the GeneClean kit (BIO101) to remove primers and heterologous fragments from the preparation.

Step 2: Subcloning PCR Fragments for Sequencing

The PCR primers from Step 1 were engineered with EcoRI restriction sites at their 5' ends to facilitate cloning of any fragments generated. An aliquot of the purified 350 bp PCR-derived fragment was digested with restriction enzyme EcoRI and ligated to the EcoRI cut phagemid vector pBSII-SK+(Stratagene). Restriction enzymes were obtained from Boehringer Mannheim Biochemicale (BMB). Digests were incubated at 37° C. for 2 hours, followed by extraction with an equal volume of phenol:chloroform:isoamyl alcohol, and ethanol precipitation. Fragments were resuspended in TE (10 mM Tris-HCl pH 8.0, 1 mM EDTA pH 8.0) and ligated together using T4 DNA Ligase (BMB). Competent JM109 bacteria were transformed with 1/5 of the ligation reaction and appropriate dilutions plated to LB+ampicillin (100 ug/ml) plates supplemented with XGal (50 ul of a 2% stock in dimethylformamide) and IPTG (10 ul of a 100 mM stock). White colonies were picked and small scale plasmid preparations performed according to the protocols listed in Sambrook et al. (1989). Plasmids were screened for the 350 bp insert by digestion with EcoRI. Several different isolates were picked, plasmid DNA isolated and purified, and subjected to DNA sequence analysis.

Step 3: Using the PCR Fragment as a CDase Specific Probe for Screening Yeast Genomic Libraries The PCR fragment obtained in Step 1 was also used as a probe for the detection of the CDase encoding sequence in screening genomic libraries for clones containing the gene. The purified fragment was labeled using alpha-$^{32}$p-dCTp and a random primer DNA labeling kit from Boehringer Mannheim Biochemicals. Yeast libraries were grown overnight in LB+amp and dilutions plated to LB+amp plates to give colony densities of 250–2000 colonies per plate. Colony lifts were performed using 0.45 um nitrocellulose circles or squares from Schliecher and Schuell. Filters were processed by placing them colony side up on Whatman 3MM paper saturated with 10% SDS for 5 minutes to fix, 0.5M NaOH, 1.5M NaCl for 5 minutes to denature, 1.5M NaCl, 0.5M TrisHcl pH 7.4 for 5 minutes to neutralize, and 2×SSC for 5 minutes prior to UV-crosslinking with a Statalinker (Stratagene), according to the manufacturer's instructions. Filters were then submerged in 2×SSC for 5 minutes and prewashed in 5×SSC, 0.5% SDS, 1 mM EDTA, at 50° C.

Prehybridization was performed in heat sealable plastic bags containing 20 ml solution per bag of 12 filters. Prehybridization solution contained 50% formamide, 6×SSC, 0.01 M NaP pH 6.8, i mM EDTA (pH 8.0), 0.5% SDS, 100 ug/ml denatured salmon sperm DNA, and 5×Denhardt's Solution. Plastic bags were submerged in a 42° C. water bath and incubated for about 12 to 16 hours. Labeled probe was purified from unincorporated nucleotides by elution from Push-Columns (Stratagens). Probe was added at approximately 10$^6$ cpm/ml fluid, and incubated for about 12 to 16 hours at 42° C. for hybridization.

Filters were washed several times in 2×SSC, 0.1% SDS at room temperature, followed by a wash in 1×SSC, 0.1% SDS at 55° C. for 1 hour. Filters were air dried, wrapped in saran wrap, and exposed overnight to X-ray film at −70° C. with intensifying screens. Autoradiographs were aligned with filters and master plates for selecting clones exhibiting a positive hybridization signal. Positive clones were rescreened by the method above twice more prior to isolation of plasmid. Plasmid DNA was isolated by growth of chloramphenicol amplified 500 ml LB+ampicillin cultures and subsequent purification using the alkaline lyeis technique as described in Sambrook et al., 1989. Some plasmids were purified by cesium chloride ethidium bromide equilibrium centrifugation, while others were eluted from PZ253 columns (5'→3') followed by precipitation with polyethylene glycol, phenol:chloroform extraction, and ethanol precipitation.

Step 4: Sequencing PCR-Derived and Genomic CDase-Encoding Clones

Several 18-mer oligonucleotides were synthesized or ordered for sequencing the DNA from PCR and genomic CDase clones. Some primers generated sequence from the coding strand, while others yielded sequence from the complementary strand. Sequencing reactions were performed according to the protocols and reagents supplied with the Sequenase Version 2.0 Kit (United States Biochemical). DNA was denatured by alkaline.denaturation in 0.2 N NaOH prior to the sequencing reactions. Dilutions of labeling reaction mix and reaction times were varied depending on the region for which sequence was desired. For most reactions, 1–1.5 pmol of template DNA and primers were used with 10–15 uCi of alpha-$^{35}$S-dATP per reaction. Samples were loaded onto 8% polyacrylamide-urea sequencing gels and run for 1–7 hours depending on the sequence to be read. Gels were fixed in 10% methanol, 10% acetic acid for 30 minutes and dried at 80° C. for 45 minutes using a Slab-Gel dryer attached to a vacuum pump. Dried gels were exposed to Kodak XAR-5 film at room temperature for 18–72 hours. Sequences were read manually. Alignment and analysis of sequence data was performed by computer using Gene Pro Software (Riverside Scientific, Seattle, Wash.). FIG. 8 shows the nucleotide sequence of genomic CDase-encoding clones. FIG. 10 shows the predicted amino acid sequence. As can be seen in the figures, the coding sequence consists of approximately 474 base pairs and specifies a protein of 158 amino acids. The predicted molecular weight of CDase so obtained is about 17,506 daltons.

Step 5: Construction of CDase-Encoding Cassettes for Expression in Yeast and Mammalian Systems The DNA sequence obtained from Step 4 was used in designing oligonucleotide primers for PCR-generated cassettes encoding CDase. Some of these oligonucleotides incorporated additional sequences such as secretory signal peptides and restriction sites for use in cloning or expression. Oligonucleotide primers were used in pairs to generate PCR fragments with the appropriate sequences added to the ends.

Specifically, a cassette encoding CDase was constructed by PCR using two primers containing both CDase specific sequence and additional sequence encoding restriction sites for cloning. The 5' primer was a 65mer containing 45 bases of sequence homologous but not completely identical to the 5' end of the genomic copy of CDase attached to a 5' tail containing the restriction sites HindIII, SalI, and NcoI. The 3' primer was a 39-mer identical to the antisense strand at the C-terminus of CDase, with an XbaI tail attached at its 5' end. The template used was the genomic clone of CDase at approximately 1 ng per reaction. Each primer was present at a concentration of 75 pmol. The PCR reactions were performed as described for Step 1.

PCR reaction products were purified by extraction with chloroform and ethanol precipitation. DNA was subsequently digested with the restriction enzymes HindIII and XbaI, subjected to gel electrophoresis, and purified by elution with GeneClean (B10101) according to the manufacturer's instructions.

Step 6: Expression Of CDase in a Mammalian System

Figure 12:
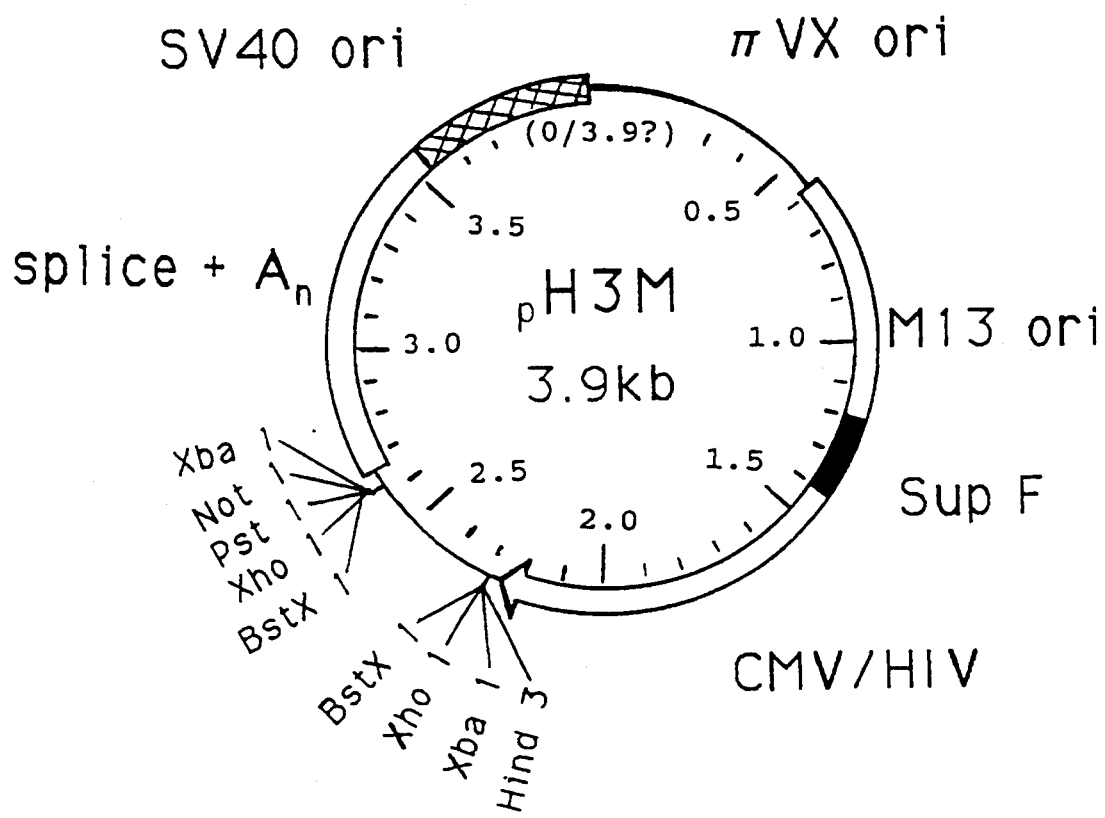
FIG. 12 shows the map of the pH3M vector.

The purified fragment from Step 5 was ligated to HindIII-XbaI digested CDM8 (ATCC Accession No. 68339) or pH3M plasmid: vector and transformed into the bacterial host MC1061 (Aruffo and Seed, 1987). A map of the pH3M vector is shown in FIG. 12. Twenty transformants were picked, small scale alkaline lysis plasmid preps performed, and aliquots digested with HindIII+XbaI to verify their structure. The remaining plasmid from three of the preparations was used for transfections of COS cells by the DEAE-Dextran transfection method (Ausubel, et al., eds. *Current Protocols in Molecular Biology*).

Briefly, $3.5 \times 10^5$ COS cells were plated to 6 cm culture dishes in DMEM/10% fetal bovine serum (FBS) and incubated overnight in 6% $CO_2$ at 37° C. DNA from the mini-preps was mixed as a cocktail with PBS and 50 mg/ml DEAE-Dextran to a total volume of 100 ul in the amounts specified below.

| Sample | DNA | FBS | DEAE-Dextran (50 mg/ml) |
|---|---|---|---|
| Controls | | | |
| Sham | 0 ul | 80 ul | 20 ul |
| BB1 | 4 ul | 76 ul | 20 ul |
| CDase Transfectants | | | |
| 1-1 | 13 ul | 67 ul | 20 ul |
| 1-4 | 13 ul | 67 ul | 20 ul |
| 2-6 | 13 ul | 67 ul | 20 ul |

Each transfection was done in duplicate. Day-old culture media were aspirated from dishes and the cells washed three times in 2 ml PBS per wash. DMEM-chloroquine transfection media were added to 1.7 ml/plate, and the DNA cocktail added dropwise to the media. Transfections were incubated for 3 hours, media removed, the cells shocked with FBS/10% DMSO for 2 minutes, washed three times in serum free media, and incubated 3 days in 3.5 ml DMEM/10% PBS per plate.

Step 7: Characterization of the Recombinant Expression Products

1. Radioimmunoprecipitations

Plates from Step 6 to be used for radioimmunoprecipitation (RIPS) were incubated for about 12 to 16 hours in fresh DMEM/10% FBS containing 200 uCi/ml $^{35}$S-methionine.

RIPS were performed by aspirating labeled media after about 12 to 16 hours incubation at 37° C., adding 1 ml 1% OG-PO4RIPAE (50 mM $Na_2HPO_4$, 1% Na-deoxycholate, 1% triton X-100, 0.1% SDS, 150 mMNaCl, 5 mM EDTA, 5 mM EGTA, 2 mM PMSF, and 1 ug/ml aprotinin=PO4-RIPAE with octoglucoside added to 1%) buffer to each culture dish, and incubating 10 minutes on ice. Lysates were transferred to 10 ml Oak Ridge centrifuge tubes and centrifuged at 40,000 rpm, 4° C. for 40 minutes Supernatants were transferred to two microfuge tubes on ice (0.4 ml/tube). The BB1 transfectants were incubated with 2 ug antibody, while 17.5 ul or 31.5 ug of rabbit antiCDase polyclonal antisera was added to the other transfectants. RIPS were incubated on ice for 1 hour. Goat antimouse was added to the BB1 tube as secondary antibody and incubated 20 minutes on ice.

Staphylococcus aureus (Calbiochem) was washed (700 ul) in 0.5% NP-40/TES buffer, then in 0.05% NP-40/TES buffer, and finally resuspended in PO4-RIPAE buffer with 1 mg/ml ovalbumin (TES=50 mM Tis-HCl, pH 7.4, 1 mM EDTA, 150 mM NaCl). Fifty microliter aliquots of washed StaphA bacteria were added to the RIP material and incubated for 10 minutes on ice. RIPS were pelleted in the microfuge and washed three times in 0.5 ml TNEN (20 mM Tris-HCl pH 8.0, 100 mM NaCl, i mM EDTA, 0.5% NP-40). The final pellets from the original 400 ul duplicate samples were resuspended in either 35 ul reducing or 35 ul nonreducing SDS-PAGE-running buffer. Samples were loaded onto a 10-20% SDS-PAGE gradient gel along with low molecular weight protein markers from Bio-Rad and electrophoresed at 300 volts for approximately 2 hours. Gels were stained in Coomassie Blue 1 hour, destained in 10% methanol, 5% acetic acid for about 12 to 16 hours, exposed to enhance for 30 minutes, then washed three times in water prior to drying at 60° C. for i hour. A 4 hour exposure of the gel to X-ray film demonstrated no 17,000 dalton band in the sham samples, no 17,000 dalton band in the BB1 samples but a specific band around 45,000 daltons in the BB1 samples, while all three transfectants exhibited a specific band at approximately 17,000 daltons.

2. Western Analysis

The duplicate transfection plates from Step 6 were left unlabeled and harvested after the three day incubation period. Media were aspirated off, cells were washed in PBS, then suspended in 0.5 ml 10 mM Tris-HCl (pH 8.0) containing I ug/ml aprotinin and 30 ug/ml PMSF. Cells were removed from the culture dishes using sterile scrapers and transferred to sterile microfuge tubes on ice. Each suspension was sonicated on ice in 2-15 second bursts at full power. The lysates were centrifuged for twenty minutes in a refrigerated microfuge to remove cell debris, and supernatants transferred to fresh tubes. Enzyme assays were performed as described below.

Aliquots from these lysates were also used to perform Western blots using the polyclonal rabbit antisera raised against purified CDase. Twenty-five microliter aliquots of undiluted transfectant lysates were subjected to SDS-PAGE electrophoresis as described for the RIPS, except that serial dilutions of purified CDase enzyme were loaded on the gel as concentration standards. Concentrated CDase at 500 ng/lane was diluted in 5-fold increments to 100 ng, 20 ng, 4 rig, and 0.8 ng/lane. The gel was then electroblotted to a nitrocellulose filter according to protocols in the CSH cloning manual (Sambrook et al., 1989).

Blots were blocked in Blotto for i hour (Blotto=PBS+1% nonfat milk+0.5% NP-40). Fresh Blotto containing 2.5 ug/ml polyclonal rabbit antiCDase sera was added to the filter and incubated at room temperature for 1 hour. The filter was washed three times for 5 minutes in Blotto, followed by an incubation in alkaline phosphatase conjugate (Boshringer Mannhelm Biochemicals) diluted 1:1000 in Blotto. Excess antibody conjugate was removed with three washes in Blotto and a final wash in alkaline phosphatase substrate buffer (100 mM Tris-HCl pH 9.5, 100 mM NaCl, 5 mM MgC12). The filter was then incubated for 15 minutes in 40 ml of the substrate buffer to which was added 12 mg bromochorindolyl phosphate and 7 mg of nitroblue tetrazolium to develop the color. Reactions were stopped by washing the filter in distilled water.

Upon color development, the three transfectants all showed bands migrating at approximately 17,000 daltons with intensities greater than the 0.8 ng and less than the 4 ng concentration standards for purified CDase.

3. Activity Measurements of Recombinantly Expressed CDase

The conversion of 5-Fluorocytosine (5-FC) to 5-Fluorouracil (5-FU) was measured in extracts from the above-transformed COS cells. Transfectants ($3\times10^5$ cells each) containing CDase (1-1, 1-4, 2-6), sham transfection, or control plasmid transfection (BB1) were sonicated in 0.5 ml 10 mMTRIS buffer and centrifuged. To 100 ul of each supernatant and a 1 ug/ml solution of CDase was added 170 ul phosphate buffered saline (PBS) and 30 ul of a 30 mM 5-FC solution. This yielded a 300 ul reaction mixture with 3 mM 5-FC. A control reaction with no enzyme was also done.

These tubes were incubated for 24 hours at 37° C., after which 50 ul of each solution was taken and the reaction quenched in i ml of 0.1 N HCl. These samples were measured on a UV spectrophotometer at 255 and 290 nm. Using the equations:

$$(0.1191 \times OD_{290} - 0.02485 \times OD_{255}) \times 20 = mM\ 5\text{-}FC$$

and $$(0.1849 \times OD_{255} - 0.04907 \times OD_{290}) \times 20 = mM\ 5\text{-}FU,$$

the amount of conversion of 5-FC to 5-FU was measured. The number of units of activity in the original cell extract was then computed (1 unit=1 umol/min conversion of 5-FC to 5--FU). The sham and BB1 transfections, and the reaction with no enzyme, yielded no activity, while all three transfectants of CDase were active. Transfectant 1-1 had $0.41\times10^{-3}$ units, 1-4 had $0.54\times10^{-3}$ units, and 2-6 had $0.26\times10^{-3}$ units. The control assay with 1 ug/ml CDase converted all of the 5-FC to 5-FU. Assuming that pure CDase has an activity of 40 U/mg, 10 ng (1-1), 13.5 ng (1-4), and 7.3 ng (2-6) of active CDase were expressed.

The same samples were also tested in an independent assay. Each assay tube included 50 ul of supernatant or 1 ug/ml CDase, 130 ul PBS, 20 ul 30 mM 5-FC, and 1 uCi [$^3$H] 5-FC. These reactions were incubated for 24 hours, evaporated to a residue redissolved in 20 ul methanol, and spotted onto silica gel thin layer chromatography (TLC) plates. Plates were developed in 96:4 acetone/water, in which the $R_f$'s for 5-FC and 5-FU are 0.2 and 0.8, respectively. The appropriate portions of the TLC plates were cut out and placed into scintillation fluid. These were counted in a scintillation counter and the relative amounts of 5-FC and 5-FU in each sample was determined. The sham and BB1 assays yielded no 5-FU, while the transfectants all converted 14% of the 5-FC to 5-FU. This translates to $0.6\times10^{-3}$ units per sample, thus confirming the amounts calculated in the UV experiment. The control reaction with 1 ug/ml CDase converted all the 5-FC to 5-FU.

Experiments show that CDase transfectants are indeed expressing active enzyme. This, coupled with the Western blot analysis, indicates that specific activity of the recombinant enzyme is similar to that isolated from yeast.

Thus, a thermally stable CDase has been disclosed as well as methods for purifying and recombinantly producing the same. Although preferred embodiments of the subject invention have been described in some detail, it is understood that this is illustrative and not limiting and that obvious variations can be made without departing from the spirit and scope of the invention as defined by the appended claims.

REFERENCES

Aruffo, A., and Seed, B., *PNAS(USA)* 84:8573–8577.
Ausubel, F. M., et al. (eds.), (1988) *Current Protocols in Molecular Biology*, (Green Publishing Associates, N.Y.).
Edge, (1981) *Nature* 292:756.
Guthrie, C., and Abelson, J., (1982) *The Molecular Biology of the Yeast Saccharomyces: Metabolism and Gene Expression*, pp. 487–528, (J. N. Strathern et al. eds., CSH).
Hellstrom, (1984) *Monoclonal Antibodies and Cancer*, pp. 31–47 (Wright et al., eds., Marcel Dekker, Inc., N.Y.).
Hellstrom, K. E., and Hellstrom, I., (1985) *Monoclonal Antibodies for Tumor Detecting and Drug Targeting*, pp. 17–51 (Baldwin et al., eds., Academic Press, N.Y.).
Hovland, P., et al., (1989) *Gene* 83:57–64.
Ipata, P.L., et al., (1971) *Biochemistry* 10:4270–4276.
Ipata, P.L and Cercignani, G. (1978) *Meth. Enz.* 51:394–401.
Jay et al. (1984) *J. Biol. Chem.* 259:6311.
Johnston, M. (1987) *Microbiol. Rev.* 51:458–476.
Katsuragi, T. (1988) Personal communication.
Katsuragi, T., et al., (1986) *Agric. Biol. Chem.* 50:1721–1730.
Katsuragi, T., et al., (1987) *App. Biochem. Biotech.* 16:61–69,
Kream, J. and Chargaff, E. (1952) *J. Amer. Chem. Soc.* 74:5157–5160.
Kunitz, M. J. (1947) *J. Gen. Physiol.* 29:393.
Malik, N., et al., (1989) MCB 2:2847–2853.
McIntosh, E. M. and Haynes, R.H. (1986) *Mol. Cell Bio.* 6:1711–1721.
Nambair et al., (1984) *Science* 223:1299.
Nishiyama, T., et al., (1985) *Cancer Res.* 45:1753–1761.
O'Donovan, G. A. and Neuhard, J. (1970) *Bact. Rev.* 34:278–343.
Sakai, T., et al., (1985) *J. Biotech.* 2:13–21.
Sakai, T., et al., (1986) *Nature* 324:163.
Sakai, T., et al., (1988) *Science* 239:487–491.
Sambrook, J., et al., *Molecular Cloning: A Laboratory Manual*, Second edition, (1989) (CSH Press).
Scharf, et al., (1986) *Science* 233:1076.
Scopes, R. K., *Protein Purification Principles and Practice*, 2nd ed. (Springer-Verlag 1987).
Senter, P.D., et al., (1987) U.S. patent application 081,382.
Stamenkovic, 1990 (in press).
Steinman, H. M. (1980) J. Biol. Chem. 255:6758–6765.
West, T. P., et al., (1982) *Biochim. Biophys. Acta* 251–258.
Yergatian, S., et al., (1977) *Experientia* 33:1570–1571.
Yeung, C. Y., et al., (1985) *J. Biol. Chem.* 260:10299–10307.

We claim:

1. An isolated nucleotide sequence encoding a thermally stable Saccharomyces cytosine deaminase having the protein sequence depicted in FIG. 10.

2. A recombinant expression vector comprising and effective in expressing the nucleotide sequence of claim 1.

3. The recombinant expression vector of claim 2 wherein the nucleotide sequence is operably linked to control sequences compatible with a procaryotic host.

4. The recombinant expression vector of claim 2 wherein the nucleotide sequence is operably linked to control sequences compatible with a eucaryotic host.

5. The recombinant expression vector of claim 4 wherein the nucleotide sequence is operably linked to control sequences compatible with a mammalian host.

6. Bacterial cells transformed with the recombinant expression vector of claim 3.

7. Mammalian cells transformed with the recombinant expression vector of claim 5.

8. A method of producing recombinant, thermally stable cytosine deaminase, or a protein functionally equivalent thereto, comprising growing the bacterial cells of claim 6.

9. A method of producing recombinant, thermally stable cytosine deaminase, or a protein functionally equivalent thereto, comprising growing the mammalian cells of claim 7.

* * * * *